(12) United States Patent
Wagle et al.

(10) Patent No.: US 6,509,480 B2
(45) Date of Patent: Jan. 21, 2003

(54) GLUCOSE AND LIPID LOWERING COMPOUNDS

(75) Inventors: Dilip R. Wagle, Nanuet, NY (US); Sheng Ding Fang, Mahwah, NJ (US); Ihor Terleckyj, Ridgewood, NJ (US); John Resek, Brooklyn, NY (US); John J. Egan, New York, NY (US)

(73) Assignee: Alteon, Inc., Ramsey, NJ (US)

( * ) Notice: Subject to any disclaimer, the term of this patent is extended or adjusted under 35 U.S.C. 154(b) by 0 days.

(21) Appl. No.: 10/047,182

(22) Filed: Oct. 23, 2001

(65) Prior Publication Data

US 2002/0151581 A1 Oct. 17, 2002

Related U.S. Application Data

(63) Continuation of application No. 09/439,706, filed on Nov. 12, 1999, now Pat. No. 6,376,396.
(60) Provisional application No. 60/295,599, filed on Nov. 12, 1998, and provisional application No. 60/198,231, filed on Nov. 20, 1998.

(51) Int. Cl.$^7$ .................. C07D 407/00; C07C 62/30
(52) U.S. Cl. .................. 549/299; 548/525; 560/126; 562/510; 562/511
(58) Field of Search .................. 548/525; 562/510, 562/511; 549/299; 560/126

(56) References Cited

U.S. PATENT DOCUMENTS

| | | | |
|---|---|---|---|
| 3,047,615 A | 7/1962 | Nomine et al. | 260/476 |
| 3,203,857 A | 8/1965 | Lucas et al. | 167/55 |
| 3,671,532 A | 6/1972 | Carraz et al. | 424/305 |
| 5,019,580 A | 5/1991 | Iwu | 514/299 |
| 5,248,221 A | 9/1993 | Gerhart et al. | 405/216 |
| 5,320,602 A | 6/1994 | Karpiel | |
| 5,397,302 A | 3/1995 | Weaver et al. | |
| 5,446,055 A | 8/1995 | Dellaria et al. | 514/337 |
| 5,478,852 A | 12/1995 | Olefsky et al. | 514/369 |
| 5,594,015 A | 1/1997 | Kurtz et al. | 514/369 |
| 5,628,999 A | 5/1997 | Luo et al. | 424/195.1 |
| 5,629,319 A | 5/1997 | Luo et al. | 514/284 |
| 5,674,900 A | 10/1997 | Ubillas et al. | 514/557 |
| 5,681,958 A | 10/1997 | Bierer | 546/70 |
| 5,691,386 A | 11/1997 | Inman et al. | 514/591 |
| 5,708,012 A | 1/1998 | Olefsky | 514/337 |
| 5,798,375 A | 8/1998 | Tsujita et al. | 514/369 |
| 5,811,242 A | 9/1998 | Iwamoto et al. | 435/7.1 |
| 5,917,084 A | 6/1999 | Jiang | |

OTHER PUBLICATIONS

Internet Article: ERCP, (NIDDK) site unknown, dated on or before Oct. 23, 2001, 3 sheets.
Internet Article: "ERCP and Stent Placement," www.gil-health.com/TREC2/scopephotos/ercp_stent, Jul. 31, 2000, 2 sheets.
Internet Article: "ERCP," www.gilhealth.com/TREC2/articles/ercp, Jul. 31, 2000, 3 sheets.
Internet Article: "ERCP," site unknown, dated on or before Oct. 23, 2001, 2 sheets.
Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438–440.
Ruzicka et al., Helvetica Chemica Acta 16:268–275 (1933).
Werner Herz et. al., Ivalin, a New Sesquiterpene Lactone, J. Org. Chem., vol. 27, pp. 905–910 (1962).
Marshall, The Structure of Alantolactone, J. Org. Chem., vol. 29, pp. 3727–3729 (1964).
Werner Herz et. al., Constituents of Iva Species. II. The Structures of Asperilin and Ivasperin, Two New Sesquiterpene Lactones, J. Org. Chem., vol. 29, pp. 1022–1026 (1964).
Werner Herz et. al., Recent Advances in Phytochemistry—Pseudoguaianolides in Compositae, Appleton–Century–Crofts, New York, vol. 1, pp. 229–269 (1968).
Werner Herz et. al., New Pseudoguaianolides From Gaillardia Pulchella, Phytochemistry, vol. 8, pp. 661–664 (1969).
H. Yoshioka et. al., Structure and Stereochemistry of Pulchellin B, C, E, and F, Journal of Organic Chemistry, vol. 35, No. 3 pp. 627–631 (1970).
Sesquiterpenoids. Part XIV. X–Ray Study of 13β–p–Bromophenylthio–11α, 13–dihydropulchellin–C Diacetate (2α, 3β–Diacetoxy–13β–p–bromo–phenylthio–11α,13–dihydroisolantolactone): Stereochemistry of Addition of Thiols to Sesquiterpenoid α–Methylene γ–Lactones, J.C.S. Perkin II, pp. 400–404 (1973).
Plant Resources, St. Petersburg, vol. 12 (1): 170–181 (1976).
Ferdinand Bohlmann et. al., Neue Sesquiterpenlactone Und Thymol–Derivate Aus Inula–Arten, Phytochemistry, vol. 16, 1243–1245 (1977).

(List continued on next page.)

*Primary Examiner*—Amelia Owens
(74) *Attorney, Agent, or Firm*—Dechert

(57) ABSTRACT

Provided are, among other things, lipid-lowering or glucose-lowering methods and compounds, particularly lipid-lowering or glucose-lowering compounds, with an A-B ring structure as follows:

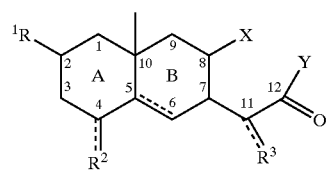

wherein the dotted line between carbons 5 and 6, the dotted line between carbon 4 and R$^2$, and the dotted line between carbon 11 and R$^3$ each independently represent an optional double bond from the respective numbered carbon to a linked carbon, and wherein X is hydroxy or, together with Y is oxy linking carbon 8 and carbon 12.

18 Claims, No Drawings

OTHER PUBLICATIONS

Yoshimoto Ohta et. al., Sesquiterpene Constituents Of Two Liverworts Of Genus Diplophyllum, Tetrahedron, vol. 33, pp. 617–628 (1977).

S.V. Govindan et. al., Transformations of Isoalantolactone & Oxidation of 8,11αH–Eudesm–4–en–8,13–olide, Indian Journal of Chemistry, vol. 16B, pp. 271–274 (1978).

Ferdinand Bohlmann et. al., New Sesquiterpene Lactones From Inula Species, Phytochemistry, vol. 17, pp. 1165–1172 (1978).

G. Fardella, Ilicic Acid from *Inula graveolens* L., Fitoterapia 50: 3–4 (1979).

Koppaka V. Rao et. al., Antibiotic Principle of Eupatorium Capillifolium, Journal of Natural Products, vol. 44, No. 3, pp. 252–256 (1981).

Johan Coetzer, Molecular and crystal structure of ivalin, S. Afr. J. Chem., 35 (3), pp. 103–104 (1982).

Ferdinand Bohlmann et. al., Sesquiterpene Lactones From Inezia Integrifolia, Phytochemistry, vol. 21, No. 11, pp. 2743–2745 (1982).

Thomas D. Rodrigues et. al., Holly Berry Ingestion: Case Report, Vet Hum Toxicol 26 (2), pp. 157–158 (1984).

Gayland F. Spencer et. al., Germination and Growth Inhibitory Sesquiterpenes From Iva Axillaris Seeds, Journal of National Products, vol. 47, No. 4, pp. 730–732 (1984).

Kiyoshi Tomioka et. al., Asymmetric Total Synthesis Of Antileukemic Sesquiterpene (+)–Ivalin, Tetrahedron Ltr., vol. 25, No. 3, pp. 333–336 (1984).

Ferdinand Bohlmann et. al., Eudesmanolides And Costic Acid Derivatives From Flourensia Macrophylla, Pergamon Press Ltd., 303A, vol. 23, No. 7, pp. 1445–1448 (1984).

Umesh C. Pandey et. al., Isoalantolactone Derivatives And Germacranolides From Blumea Densiflora, Phytochemistry, vol. 24, No. 7, pp. 1509–1514 (1985).

Handbook of Effective Ingredients of Medicinal Plants, National Medical Administration, Beijing (1986).

S.M. Adekenov et. al., Izvestia Academy Science Kazakhstan (Izv. Akad. NavkkazSSR), Chemistry Series, vol. 5, pp. 74–79 (1986).

A. Rustaiyan et. al., Further Sesquiterpene Lactones From The Genus Dittrichia, Phytochemistry, 303A, vol. 26, No. 9, pp. 2603–2606 (1987).

*Helenii rhizoma*, Elecampane, pp. 254–256 (1990).

Simoes et al., Constituents of Dittrichia Viscose Subsp. Viscosce, Fitoterapia, vol. LXI, No. 6, pp. 553–554 (1990).

S.M. Adekenov et. al., Pulchellin C From *Inula caspica*, Chemistry of Natural Compounds, vol. 26, No. 3, pp. 338 (1990).

S.M. Adekenov et. al, Pulchellin C and Inuchinenolide C From *Inula caspica*, Chemistry of Natural Compounds, vol. 26, No. 1, pp. 635–642 (1990).

A. Ulubelen, Sesquiterpene Acids From Echinops Ritro, Fitoterapia, vol. LXII, No. 3, pp. 280 (1991).

Rosa Lanzetta et. al., Ichthyotoxic Sesquiterpenes And Xanthanolides From Dittrichia Graveolens, Phytochemistry, vol. 30, No. 4, pp. 1121–1124 (1991).

Gonzalo Blay et. al., Synthesis of (+)—Isoalantolactone and (+)—Isoalloalantolactone from (–)—Santonin, Tetrahedron Ltr., vol. 48, No. 25, pp. 5265–5272 (1992).

P.R.H. Moreno et. al., Chemical Constituents and Antitumor Activity of *Nectandra grandiflora*, Int. J. Pharmacog., 31, No. 3, pp. 189–192 (1993).

Gulacti Topcu et. al., Cytotoxic And Antibacterial Sesquiterpenes From *Inula Graveolens*, Phytochemistry, vol. 33, No. 2, pp. 407–410 (1993).

Koblandy M. Turdybekov et. al., Conformation of the α–Methylene–γ–lactone Ring and Violation of Geissman's Rule in Sesquiterpene Lactones, Mendeleev Commun., pp. 42–44 (1995).

Elzbieta Hejchman et. al., Synthesis and Cytotoxicity of Water–Soluble Ambrosin Prodrug Candidates, J. Med. Chem., 38, pp. 3407–3410 (1995).

Registry 84078–148, ACS 1996.

GLUCOSE AND LIPID LOWERING COMPOUNDS

This application is a continuation of U.S. application Ser. No. 09/439,706, filed Nov. 12, 1999, now U.S. Pat. No. 6,326,396, which in turn claims priority of U.S. Provisional Application No. 60/295,599 filed Nov. 12, 1998 and U.S. Provisional Application No. 60/198,231 filed Nov. 20, 1998.

The present invention relates to methods of reducing hyperlipidemia and hyperglycemia, as well as to certain compounds and compositions.

The adverse complications of hyperlipidemia are prevalent worldwide, manifest by the high incidence of serious atherosclerotic disease including heart attack and stroke. Cardiovascular and cerebrovascular disease are slowly progressive conditions, often undetected in their early stages of pathophysiology, that are typified by elevated circulating levels of lipids and demonstrable by the accumulating deposition of fatty substances in the macrovasculature over years to decades. Only when sufficient vascular damage and accumulated thrombotic material is present to occlude a major vessel or become detached and create a vascular obstruction, does this disease wreak its high incidence of morbidity and mortality.

Underlying factors both within and beyond an individual's control contribute to the disease process, including genetic predisposition, co-morbidity with diseases such as diabetes mellitus, or lifestyle factors including diet, smoking, and exercise, among other factors. While genetic components have only recently become potential direct targets for therapeutic intervention, and alterations in lifestyle are difficult to achieve and often difficult to maintain, therapies directed toward pharmacologically lowering circulating lipid levels have been clinically successful at reducing the incidence of cardiovascular and cerebrovascular disease. Elevated circulating lipids and their markers indicative of a pathological state include free fatty acids, glycerol, triglycerides, cholesterol, and low-density lipoprotein. Reduction or control of each of these components can have a positive impact upon other abnormal circulating analytes, including glucose and insulin.

Diabetes mellitus is a disease of multifactorial origins involving disorders of metabolism associated with insulin-producing as well as insulin-regulated tissues. In addition to being a disease of hyperglycemia, some forms of the disease are associated with abnormally elevated circulating lipid levels, Therefore, lowering the circulating levels of lipids and glucose is beneficial for the treatment of patients with diabetes mellitus. In type II diabetes, while genetic mutations can cause certain subsets of the disease (e.g., maturity-onset diabetes of the young, or MODY), the most common form of the disease involves resistance to the action of insulin on insulin-target tissues, and is associated with obesity, predominately of abdominal origin. In addition to elevated glucose levels, circulating levels of triglycerides, cholesterol and non-esterified fatty acids (NEFA) are elevated during a fasting period. Persons afflicted with diabetes are predisposed to the development of cardiovascular disorders, which is the main cause of morbidity and mortality for this disease. Resistance to insulin action occurs not only in hyperglycemic states but also in Syndrome X, an insulin-resistant disorder characterized by hyperinsulinemia and dyslipidemia. (Reaven GM, Syndrome X, Clinical Diabetes, March/April 1994:32–36). In this state, normoglycemia can be maintained due to an increase in the secretion of insulin. However, when the insulin-resistance cannot be sustained by the compensatory activity of the pancreas, glucose-intolerance supervenes. Thus, lipid abnormalities, coupled either with overt hyperglycemia or with the normoglycemic Syndrome X phenotype, are believed to contribute to the severity of diabetic complications, such as cardiovascular complications (Olefsky, JM, Current Approaches to the Management of Type 2 Diabetes: A Practical Monograph, National Diabetes Education Initiative, 1997).

Oral antihyperglycemic agents, such as the sulfonylureas and biguanides, promote improvements in elevated lipid levels through overcoming the associated state of insulin-resistance, either by potentiating the endogenous release of insulin from the β cells of the pancreas, as in the case of the sulphonylureas, or by enhancing glucose disposal and reducing gluconeogenesis, as in the case of biguanides. Other approaches to controlling the elevated lipids and glucose have involved the use of broad acting oral antihyperglycemics such as the thiazolidinedione class of agents which lower fatty acids and improve the insulin-resistant state of insulin responsive tissues. The compound 4,7,8αH-eudesma-5(6),11(13)-dien-8,12-olide, also known as helenin and alantolactone, has been reported to induce hyperglycemia in rabbits at high dose, to induce hypoglycemia at a moderate dose, and to inhibit hyperglycemia induced by food (1986, Handbook of Effective Ingredients of Medicinal Plants, Beijing, China).

Numerous, diverse therapeutic strategies have been developed for treating the hyperlipidemia and associated hyperglycemia of type II diabetes. The aim of lowering of circulating lipids has been to reduce the cardiovascular morbidity and/or improving the overall diabetic state, Examples of classes of agents acting directly on plasma triglyceride and cholesterol content include the HMG-CoA reductase inhibitors, fibric acids, and bile-salt resins. Whereas these classes are effective in lowering triglyceride and cholesterol content, they have little impact on plasma fatty acids.

Of the lipid classes, non-esterified fatty acids appear to play a role in promoting the diabetic and/or the hyperlipidemic, insulin-resistant, state. Elevated free fatty acids arise from either the excess body burden of adipose tissue in the obese state or from uncontrolled breakdown of triglycerides in adipose tissue, a major insulin-target tissue, or both. In addition, elevated levels of free fatty acids have been shown to acutely induce insulin resistance in muscle, the major glucose utilizing tissue of the body, where a direct effect on glucose transport in muscle is observed. In addition, fatty acids affect liver metabolism to increase hepatic glucose output. Furthermore, elevated fatty acids induce impaired α-cell functioning by lessening the secretion of insulin from α-cells in response to a glucose stimulus. Attempts to reduce fatty acid levels have included the development of thermogenic agents (?3 agonists) which are believed to function by stimulating brown adipose tissue to oxidize fatty acids and thus clear them from the circulation. Alternatively, removing fatty acids from their influence in the liver was attempted by developing inhibitors of fatty acid oxidation by the enzyme carnitine palmitoyl transferase I (CPTI).

In particular, resistance to the action of insulin in adipose tissue appears to plays a significant role in the elevation of fatty acids. Agents that inhibit adipose tissue breakdown of triglycerides are known as lipolytic inhibitors. It is toward the development of new methods and agents for lowering circulating lipids to treat hyperlipidemic disorders or for lowering circulatory glucose to treat hyperglycemia, diabetes and associated disorders that the present invention is directed.

SUMMARY OF THE INVENTION

The invention relates to lipid-lowering or glucose-lowering methods and compounds, particularly lipid-lowering or glucose-lowering compounds, with an A-B ring structure of the following Formula I:

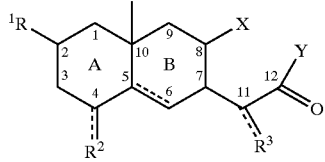

I wherein the dotted line between carbons 5 and 6, the dotted line between carbon 4 and $R^2$, and the dotted line between carbon 11 and $R^3$ each independently represent an optional double bond from the respective numbered carbon to a linked carbon.

The present invention to provides, among other things: methods for lowering lipid levels in a mammal to treat or prevent the development of pathology associated with elevated lipid levels; compounds which inhibit the enzyme hormone-sensitive lipase and inhibit lipolysis; agents and methods for the treatment of insulin resistance and Syndrome X; methods for lowering glucose levels in a mammal in order to treat or prevent the development of pathology associated with hyperglycemia; methods for treating impaired glucose tolerance associated with fasting or prandial hyperglycemia, normoglycemia, or insulin resistance, for example to delay or prevent the onset of non-insulin-dependent diabetes mellitus.

DETAILED DESCRIPTION

In accordance with the present invention, methods for lowering lipid levels in a mammal or lowering glucose levels in a mammal (particularly a hyperglycemic mammal) are provided comprising administering to said mammal an effective amount of a composition comprising a compound of the formula:

The invention relates to a method for lowering blood lipid levels or lowering blood glucose in a mammal comprising administering to the mammal a lipid-lowering or glucose-lowering effective amount of one or more compounds with an A-B ring structure, the compounds of Formula I, wherein the dotted line between carbons 5 and 6, the dotted line between carbon 4 and $R^2$, and the dotted line between carbon 11 and $R^3$ each independently represent an optional double bond from the respective numbered carbon to a linked carbon, wherein $R^1$ is hydrogen, hydroxy, a lower alkanoyloxy or an aroyloxy group (wherein aryl of aroyloxy can be substituted by one or more lower alkyl, lower alkoxy, halo, trifluoromethyl, di(lower)alkylamino, hydroxy, nitro or C1–C3 alkylenedioxy groups); wherein X is hydroxy or, together with Y is oxy linking carbon 8 and carbon 12; wherein Y is hydroxy or an amino group that can be mono or di-substituted with lower alkyl, where the lower alkyls can be joined to form a five or six-membered ring; wherein $R^2$ and $R^3$ are each independently a lower alkyl or alkenyl group, wherein the lower alkyl of $R^3$ can be substituted at the carbon linked to C11 with an amino group that can be mono or di-substituted with lower alkyl, where the lower alkyls can be joined to form a five or six-membered ring, or pharmaceutically acceptable salts thereof, with the proviso that where $R^1$ is hydrogen, either (a) X is hydroxy or (b) $R^3$ is substituted with amino. The invention further relates to the administered pharmaceutical composition.

The invention also relates to a compound (and pharmaceutical compositions thereof) of Formula I, wherein the dotted line between carbons 5 and 6, the dotted line between carbons 4 and $R^2$, and the dotted line between carbon 11 and $R^3$ each independently represent an optional double bond from the respective numbered carbon to a linked carbon wherein $R^1$ is hydrogen, hydroxy, a lower alkanoyloxy or an aroyloxy group (wherein aryl of aroyloxy can be substituted by one or more lower alkyl, lower alkoxy, halo, trifluoromethyl, di(lower)alkylamino, hydroxy, nitro or C1–C3 alkylenedioxy groups); wherein X is hydroxy or, together with Y is oxy linking carbon 8 and carbon 12; wherein Y is hydroxy or an amino group that can be mono or di-substituted with lower alkyl, where the lower alkyls can be joined to form a five or six-membered ring; wherein $R^2$ and $R^3$ are each independently a lower alkyl or alkenyl group, wherein the lower alkyl of $R^3$ can be substituted with an amino group that can be mono or di-substituted with lower alkyl, where the lower alkyls can be joined to form a five or six-membered ring, or pharmaceutically acceptable salts thereof, with the provisos that (1) where X is hydroxy, then $R^1$ is not hydrogen, (2) where $R^1$ is hydroxy, then X is either (a) X is hydroxy or (b) $R^3$ is substituted with amino, and (3) where $R^2$ is methylene linked to C4 by a double bond, $R^3$ is methylene linked to C11 by a double bond, and X is oxy, then $R^1$ is not ethanoyloxy. Preferably, $R^1$ is not propanoyloxy.

In one embodiment, the hydrogen substituents at positions 5, 7 and 8 are alpha relative to the A-B ring structure. In another embodiment, X is hydroxy. In another embodiment, $R^1$ is a lower alkanoyloxy group, for example, selected from the group consisting of acetoxy, propanoyloxy, isobutyryloxy, and cyclopropanoyloxy. The compound is, for example, selected from the group consisting of 2α-acetoxy-5,7,8αH-eudesma-4(15),11(13)-dien-8,12-olide; 2α-propanoyloxy-5,7,8αH-eudesma-4(15),11(13)-dien-8,12-olide; 2α-cyclopropanoyloxy-5,7,8αH-eudesma-4(15),11(13)-dien-8,12-olide; 2α-acetoxy-4,5,7,8,11αH-eudesman-8,12-olide; 2α-cyclopropanoyloxy-5,7,8,11αH-eudesm-4(15)-en-8,12-olide. In another embodiment, R1 is a aroyloxy group, such as furoyloxy and benzoyloxy, for example, 2α-benzoyloxy -5,7,8αH-eudesma-4(15),11(13)-dien-8,12-olide; 2α-furoyloxy-5,7,8αH-eudesma-4(15),11(13)-dien-8,12-olide, 2α-benzoyloxy-4,5,7,8,11αH-eudesman-8,12-olide; or 2α-benzoyloxy-5,7,8,11αH-eudesm-4(15)-en-8,12-olide.

The compounds can be administered in a lipid-lowering effective amount or a a glucose-lowering effective amount.

In one embodimemt, (1) X is oxy, (2) $R^1$ is lower alkanoyloxy or aroyloxy, with the proviso that when $R^2$ is methylene linked to C4 by a double bond, $R^3$ is methylene linked to C11 by a double bond, then $R^1$ is not ethanoyl, and (3) wherein $R^2$ and $R^3$ are each independently a lower alkyl group or a lower alkenyl group with the unsaturation limited to the linkage to carbon 4 or carbon 11. In another embodiment, (1) X is oxy, (2) $R^1$ is lower alkanoyloxy or aroyloxy, and (3) wherein $R^2$ and $R^3$ are each independently a lower alkyl group or a lower alkenyl group with the unsaturation limited to the linkage to carbon 4 or carbon 11.

The lower alkyl and alkenyl groups contain one to six carbons. Lower alkenyl groups are defined in conjunction with the backbone structures of Formula I, such that a methylene group has its unsaturation in conjunction with, for example, carbon 4 or carbon 11. In one embodiment, at least one or both of $R^1$ and $R^2$ are methyl or methylene (both bonds in a double bond to carbon 4 or carbon 11). The lower alkanoyloxy groups referred to above contain one or two to six carbon atoms and include methanoyloxy, ethanoyloxy or acetoxy, propanoyloxy, butyryloxy, pentanoyloxy, hexanoyloxy, and the corresponding branched-chain isomers thereof Also included among the alkanoyloxy groups herein are those comprising substituted and unsubstituted cycloalkyl groups, such as cyclopropanoyloxy, cyclobutanoyloxy, cyclopentanoyloxy, cyclohexanoyloxy, 1-methylcyclohexanoyloxy, trans-4-isopropylcyclohexanoyloxy, and the like. The aroyloxy groups referred to herein include substituted and unsubstituted aromatic and heteroaromatic groups such as furoyloxy, benzoyloxy, 4-fluorobenzoyloxy, 2-chlorobenzoyloxy, 2-methoxybenzoyloxy, 3-ethylbenzoyloxy, 4-ethylbenzoyloxy, 4-isopropylbenzoyloxy, 4-chlorobenzoyloxy, 3,5-tert-dibutyl-4-hydroxybenzoyloxy, 2-methoxy-5-chlorobenzoyloxy, 3-fluoro-4'-methoxybenzoyloxy, 2-trifluoromethylbenzoyloxy, 4-trifluoromethylbenzoyloxy, 2-naphthoyloxy, 2-thiophenecarbonyloxy, 3-pyridinecarbonyloxy, and 5-methyl-2'-pyrazinecarbonyloxy. Both the $2\alpha$ and $2\beta$ isomers are included, $2\alpha$ is preferred. The lower alkyl groups include methyl, ethyl, propyl, butyl, pentyl, heyxl, and the corresponding brnached-chain isomers thereof Preferably, the aryl groups are C6–C10 aromatic groups, or a heteroaromatic groups with 5 to 10 ring atoms, of which, preferably, up to two (2) are heteroatoms selected from nitrogen, oxygen or sulfur.

The lower alkyl groups referred to above include methyl, ethyl, propyl, butyl, pentyl, hexyl, and the corresponding branched-chain isomers thereof As described above, the bond linking groups $R^2$ and $R^3$ can be a single or double bond, and the alkyl groups described herein can be bonded to carbons 4 and 11, respectively, by means of a single or double bond.

Non-limiting examples of compounds in which $R^1$ is hydrogen include salts, such as sodium salts, of: 8β-hydroxy-4,7,8αH-eudesama-5,11(13)-dien-12-oic acid; 8,β-hydroxy-5,7,8,11αH-eudesam-4(15)-en-12-oic acid; 8β-hydroxy-4,5,7,8,11αH-eudesman-12-oic acid; 2α-hydroxy-4(15),11(13)eudesmadien-12,8-olide. Non-limiting examples of compounds in which $R^1$ is hydroxy include salts, such as sodium or hydrochloride salts, of: 2α,8β-dihydroxy-2β-4,5,7,8,11αH-eudesaman-12-oic acid; 2α,8β-dihydroxy-4(15)11(13)-eudesamadien-12-oic acid; 2α-benzoyl-8β-hydroxy-2β, 4, 5, 7, 8, 11αH-eudesaman-12-oic acid; 1-[2α-hydroxy-11,12-dihydro-5,7,8αH-eudesm-4(15)-en-8,12-olidyl]-pyrrolidine; and 1-[2α-benzoyloxy- 11,12-dihydro-5,7,8αH-eudesm4(15)-en-8,12-olidyl]-pyrrolidine.

Compounds in which $R^1$ is a lower alkanoyloxy group include but are not limited to 2α-acetoxy-5,7,8αH-eudesma-4(15),11(13)-dien-8,12-olide; 2α-propanoyloxy-5,7,8αH-eudesma-4(15),11(13)-dien-8,12-olide; 2α-isobutyryloxy-5,7,8αH-eudesma-4(15),11(13)-dien-8,12-olide; α-cyclopropanoyloxy-5,7,8αH-eudesma-4(15),11(13)-dien-8,12-olide; 2α-acetoxy-4,5,7,8,11αH-eudesman-8,12-olide; and 2α-cyclopropanoyloxy-5,7,8,11αH-eudesama-4(15)-en-8,12-olide. Compounds in which R1 is a aroyloxy group include. for example, 2α-benzoyloxy-5,7,8αH-eudesma-4(15),11(13)-dien-8,12-olide,2α-furoyloxy-5,7,8αH-eudesma-4(15),11(13)-dien-8,12-olide; 2α-benzoyloxy-4,5,7,8,11αH-eudesman-8,12-olide; and 2α-benzoyloxy-5,7,8,11αH-eudesm-4(15)-en-8,12-olide.

The compounds of the present invention, upon administration to hyperlipidemic mammals, exact positive effects on circulating lipid levels. Furthermore, in vitro, the compounds specifically inhibit an enzyme, hormone-sensitive lipase (HSL), and inhibit lipolysis in a whole-cell model. In vivo, the compounds described herein inhibit the appearance of increased circulating free fatty acids in overnight fasted normal mice. In genetic models of obesity/type II diabetes associated with hyperlipidemia, the compounds reduce elevated circulating lipid levels.

The compounds of the present invention are prepared from synthetic starting materials or those isolated from natural sources. One particular starting material with double bonds between carbons 4 and 15, and between carbons 11 and 13,2α-hydroxy-5,7,8αH-eudesma4(15),11(13)-dien-8, 12-olide, can be synthesized by the procedure described by Tomioka et al. (1984, *Tetrahedron Letters* 25:333–336) or isolated and purified from the plant *Iva microcephala* or other plants, as described by Herz et al. (1962,*J Org. Chem.* 27:905–910). The alkanoyloxy and aroyloxy derivatives of 2-hydroxy compounds, such as 2α-hydroxy-5,7,8αH-eudesma-4(15),11(13)dien-8,12-olide, are prepared by synthetic procedures known to one of ordinary skill; for example, 2α-propanoyloxy-5,7,8αH-eudesma-4(15),11 (13)-dien-8,12-olide and 2α-benzoyloxy-5,7,8αH-eudesma-4(15),11(13)dien-8,12-olide are prepared from 2(α-hydroxy-5,7,8αH-eudesm-4(15),11(13)-dien-8,12-olide by reaction with propanecarbonyl chloride and benzoyl chloride, respectively. To prepare the compounds of the present invention that have single bonds between R2 and R3 and the respective ring carbon, a dien such as 2α-hydroxy-5,7,8αH-eudesm-4(15),11(13)-dien-8,12-olide is first reduced to 2α-hydroxy-4,5,7,8,11αH-eudesman-8,12-olide, for example following the procedure of Herz et al. (1962,*J Org. Chem.* 27:905–910), and then reacted with, for example, acyl chloride or benzoyl chloride, to yield 2α-acetoxy-4,5,7,8,11αH-eudesman-8,12-olide and 2α-benzoyloxy-4,5,7,8,11αH-eudesman-8,12-olide, respectively. Those compounds wherein only one of $R^2$ or $R^3$ is double-bonded to the ring can be isolated or prepared by synthesis or from natural sources, followed by synthetic procedures similar to those described above For example compounds 5,7,8αH-eudesma-4(15),11(13)-dien-8,12-olide, 4,7,8αH-eudesma-5(6),11(13)-dien-8,12-olide and 5,7,8,11αH-eudesm-4(15)-en-8,12-olide can be isolated from 80% isohelenin (which is available from Sigma Chemical Co., St. Louis, Mo., USA) by silica gel chromatography (e.g., loading with petroleum, ether, eluting with increasing concentrations of ethyl ether). 4,5,7,8,11αH-eudesman-8,12-olide can be prepared by the reduction of 4,7,8αH-eudesma-5(6),11(13)-dien-8,12-olide.

A useful source of compounds or starting materials are the plant isolates described by numerous authors including: Bohlmann et al., "New Sesquiterpene Lactones from *Inula* Species," 1978, *Phytochem.* 17:1165–1172, Topcu et al., "Cytotoxic and Antibacterial Sesquiterpenes from *Imula Graveolens,"* 1993, *Phytochem.* 33:407–410, Ohta et al., "Sequiterpene Constituents fo Two Liverworts of Genus Diplophyllum, 1977, *Tetrahedron* 33:617–628; Herz et al., 1964, "Constituents of Iva Species II," *J Org. Chem.* 29:1022–1026.

Compounds where $R^3$ incorporates an amino can be synthesized by Michael addition, such as the analogous such additions described in Hejchman et al. (1995, 38:3407–3410). Open ring compounds can be synthesized by hydrolysis of the corresponding lactone.

Typical synthetic procedures are described in the Examples, below. Both the $2\alpha$ and $2\beta$ isomers are included; $2\alpha$ is preferred. The $2\beta$ isomer can be prepared from the corresponding $2\alpha$ isomer using the Mitsunobu reaction (Mitsunobu et al., 1967, Bull. Chem. Soc. Japan 40:935).

Representative compounds of the present invention include:

2α-cyclohexanecarbonyloxy-4,5,7,8,11αH-eudesman-8,12-olide
2α-cyclopentanecarbonyloxy-4,5,7,8,11αH-eudesman-8,12-olide
2α-cyclobutanecarbonyloxy-4,5,7,8,11αH-eudesman-8,12-olide
2α-(2'-naphthoyloxy)5,7,8,11αH-eudesm-4(15)-en-8,12-olide
2α-(1'-methylcyclohexanecarbonyloxy)-5,7,8αH-eudesma-4(15),11(13)-dien-8,12-olide
2α-(4'-trifluoromethylbenzoyloxy)-4,5,7,8,11αH-eudesman-8,12-olide
2α-(2'-naphthoyloxy)-4,5,7,8,11αH-eudesman-8,12-olide
2α-cyclohexanecarbonyloxy-5,7,8αH-eudesma-4(15),11(13)-dien-8,12-olide
2α-(3',5'-di-tert-butyl-4'-hydroxybenzoyloxy)5,7,8,11αH-eudesm-4(15)-en-8,12-olide
2α-(2'-methoxy-5'-chlorobenzoyloxy)-4,5,7,8,11αH-eudesman-8,12-olide
2α-(trans-4'-isopropylcyclohexanecarbonyloxy)-5,7,8αH-eudesma-4(15),11(13)-dien-8,12-olide
2α-cyclopentanecarbonyloxy-5,7,8αH-eudesma-4(15),11(13)-dien-8,12-olide
2α-(4'-ethylbenzoyloxy)5,7,8,11αH-eudesm-4(15)-en-8,12-olide
2α-(3'-ethylbenzoyloxy)5,7,8,11αH-eudesm-4(15)-en-8,12-olide
2α-cyclobutanecarbonyloxy-5,7,8αH-eudesma-4(15),11(13)-dien-8,12-olide
2α-(2'-methoxybenzoyloxy)5,7,8,11αH-eudesm-4(15)-en-8,12-olide
2α-(2'-trifluoromethylbenzoyloxy)-5,7,8,11αH-eudesm-4(15)-en-8,12-olide
2α-(3'-fluoro-4'-methoxybenzoyloxy)-5,7,8,11αH-eudesm-4(15)-en-8,12-olide
2α-(2'-methoxy-5'-chlorobenzoyloxy)5,7,8,11αH-eudesm-4(15)-en-8,12-olide
2α-(2α-(2'-chlorobenzoyloxy)-5,7,8,11αH-eudesm-4(15)-en-8,12-olide
2α-(4'-fluorobenzoyloxy)-5,7,8,11αH-eudesm4(15)-en-8,12-olide
2α-(trans-4'-isopropylcyclohexanecarbonyloxy)-5,7,8αH-eudesma-4(15),11(13)-dien-8,12-olide
2α-(1'-methylcyclohexanecarbonyloxy)-5,7,8αH-eudesma-4(15),11(13)-dien-8,12-olide
2α-(4-fluorobenzoyloxy)-4,5,7,8,11αH-eudesman-8,12-olide
2α-(2α-(2'-chlorobenzoyloxy)-4,5,7,8,11αH-eudesman-8,12-olide
2α-(2'-methoxybenzoyloxy)-4,5,7,8,11αH-eudesman-8,12-olide
2α-(3'-ethylbenzoyloxy)-4,5,7,8,11αH-eudesman-8,12-olide
2α-(4'-ethylbenzoyloxy)-4,5,7,8,11αH-eudesman-8,12-olide
2α-(4'-isopropylbenzoyloxy)-4,5,7,8,11αH-eudesman-8,12-olide
2α-(4'-chlorobenzoyloxy)-4,5,7,8,11αH-eudesman-8,12-olide
2α-(3',5'-tert-dibutyl-4'-hydroxybenzoyloxy)-4,5,7,8,11αH-eudesman-8,12-olide
2α-(2'-naphthoyloxy)-5,7,8αH-eudesma-4(15),11(13)-dien-8,12-olide
2α-(3'-fluoro-4'-methoxybenzoyloxy)-4,5,7,8,11αH-eudesman-8,12-olide
2α-(2'-trifluoromethylbenzoyloxy)-4,5,7,8,11αH-eudesman-8,12-olide
2α-(4'-isopropylbenzoyloxy)- 5,7,8,11αH-eudesm-4(15)-en-8,12-olide
2α-(4'-chlorobenzoyloxy)5,7,8,11αH-eudesm-4(15)-en-8,12-olide
2α-cyclohexanecarbonyloxy-5,7,8αH-eudesma-4(15),11(13)-dien-8,12-olide
2α-cyclopentanecarbonyloxy-5,7,8αH-eudesma-4(15),11(13)-dien-8,12-olide
2α-(4'-trifluoromethylbenzoyloxy)-5,7,8,11αH-eudesm-4(15)-en-8,12-olide
2α-cyclobutanecarbonyloxy-5,7,8αH-eudesma-4(15).11(13)-dien-8,12-olide
2α-(1'-methylcyclohexanecarbonyloxy)-4,5,7,8,11αH-eudesman-8,12-olide
2α-(trans-4'-isopropylcyclohexanecarbonyloxy)-4,5,7,8,11αH-eudesman-8,12-olide
2α-(4'-fluorobenzoyloxy)-5,7,8αH-eudesma-4(15),11(13)-dien-8,12-olide
2α-(2α-(2'-chlorobenzoyloxy)-5,7,8αH-eudesma-4(15),11(13)-dien-8,12-olide
2α-(2'-methoxybenzoyloxy)-5,7,8αH-eudesma-4(15),11(13)-dien-8,12-olide
2α-(3'-ethylbenzoyloxy)-5,7,8αH-eudesma-4(15),11(13)-dien-8,12-olide
2α-(4'-ethylbenzoyloxy)-5,7,8αH-eudesma-4(15),11(13)-dien-8,12-olide
2α-(4'-isopropylbenzoyloxy)-5,7,8αH-eudesma-4(15),11(13)-dien-8,12-olide
2α-(4'-chlorobenzoyloxy)-5,7,8αH-eudesma-4(15),11(13)-dien-8,12-olide
2α-(3',5'-tert-dibutyl-4'-hydroxybenzoyloxy)-5,7,8αH-eudesma-4(15),11(13)-dien-8,12olide
2α-(2'-methoxy-5'-chlorobenzoyloxy)-5,7,8αH-eudesma-4(15),11(13)-dien-8,12-olide
2α-(3'-fluoro-4'-methoxybenzoyloxy)-5,7,8αH-eudesma-4(15),11(13)-dien-8,12-olide
2α-(2'-trifluoromethylbenzoyloxy)-5,7,8αH-eudesma-4(15),11(13)-dien-8,12-olide
2α-(4'-trifluoromethylbenzoyloxy)-5,7,8αH-eudesma-4(15),11(13)-dien-8,12-olide
2α-benzoyloxy4,5,7,8,11αH-eudesman-8,12-olide
2α-benzoyloxy-5,7,8αH-eudesma-4(15),11(13)-dien-8,12-olide
2α-benzoyloxy-5,7,8,11αH-eudesm-4(15)-en-8,12-olide
2β-benzoyloxy-4,5,7,8,11αH-eudesman-8,12-olide
2β-benzoyloxy-5,7,8αH-eudesma-4(15),11(13)-dien-8,12-olide
2β-benzoyloxy-5,7,8,11αH-eudesm-4(15)-en-8,12-olide
2α-cyclopropanoyloxy-4,5,7,8,11αH-eudesman-8,12-olide
2α-cyclopropanoyloxy-5,7,8,11αH-eudesm-4(15)-en-8,12-olide
2α-cyclopropanoyloxy-5,7,8αH-eudesma-4(15),11(13)-dien-8,12-olide
2β-cyclopropanoyloxy-4,5,7,8,11αH-eudesman-8,12-olide
2β-cyclopropanoyloxy-5,7,8,11αH-eudesm-4(15)-en-8,12-olide
2β-cyclopropanoyloxy-5,7,8αH-eudesma-4(15),11(13)-dien-8,12-olide
2α-furoyloxy-5,7,8αH-eudesma-4(15),11(13)-dien-8,12-olide
2α-furoyloxy-5,7,8,11αH-eudesm-4(15)-en-8,12-olide
2α-furoyloxy-4,5,7,8,11αH-eudesman-8,12-olide
2β-furoyloxy-5,7,8αH-eudesma-4(15),11(13)-dien-8,12-olide
2β-furoyloxy-5,7,8,11αH-eudesm-4(15)-en-8,12-olide 2β-furoyloxy-4,5,7,8,11αH-eudesman-8,12-olide
2α-isobutyryloxy-5,7,8,11αH-eudesm-4(15)-en-8,12-olide
2α-isobutyryloxy-4,5,7,8,11αH-eudesman-8,12-olide
2α-isobutyryloxy-5,7,8αH-eudesma-4(15),11(13)-dien-8,12-olide
2β-isobutyryloxy-5,7,8,11αH-eudesm-4(15)-en-8,12-olide
2β-isobutyryloxy-4,5,7,8,11αH-eudesman-8,12-olide
2β-isobutyryloxy-5,7,8αH-eudesama-4( 15),11(13)-dien-8,12-olide
2α-propanoyloxy4,5,7,8,11αH-eudesman-8,12-olide
2α-propanoyloxy-5,7,8,11αH-eudesm-4(15)-en-8,12-olide
2α-propanoyloxy-5,7,8αH-eudesma-4(15),11(13)-dien-8,12-olide
2β-propanoyloxy-4,5,7,8,11αH-eudesman-8,12-olide
2β-propanoyloxy-5,7,8,11αH-eudesm-4(15)-en-8,12-olide
2β-propanoyloxy-5,7,8αH-eudesma-4(15),11(13)-dien-8,12-olide
2α-acetoxy-5,7,8αH-eudesma-4(15),11(13)-dien-8,12-olide
2α-acetoxy-5,7,8,11αH-eudesm-4(15)-en-8,12-olide
2α-acetoxy-4,5,7,8,11αH-eudesman-8,12-olide
2β-acetoxy-5,7,8αH-eudesma4(15),11(13)-dien-8,12-olide
2β-acetoxy-5,7,8,11αH-eudesm-4(15)-en-8,12-olide
2β-acetoxy-4,5,7,8,11αH-eudesman-8,12-olide
4,5,7,8,11αH-eudesman-8,12-olide
4,7,8αH-eudesma-5(6),11 (13)-dien-8,12-olide
5,7,8αH-eudesma-4(15),11(13)-dien-8,12-olide
5,7,8,11αH-eudesm-4(15)-en-8,12-olide
2α-hydroxy-4(5),11(13)eudesmadien-12,8-olide
1-[sodium2α-benzoyloxy-8β-hydroxy-11,13-dihydro-5,7,8,11αH-eudesm-4(13)en- 12-oatyl]-pyrrolidine hydrochloride
sodium8β-hydroxy-4,5,7,8,11αH-eudesman-12-oate
sodium8β-hydroxy-5,7,8αH-eudesma-4(15),11(13)-dien-12-oate
sodium 8β-hydroxy-4,7,8αH-eudesma-5(6),11(13)-dien-12-oate
sodium 8β-hydroxy-5,7,8,11αH-eudesm-4( 15)-en-12-oate
sodium 2α,8β-dihydroxy-2β-4,5,7,8,11αH-eudesman-12-oate
sodium 2α,8β-dihydroxy-4(15),11(13 )-eudesmadien-12-oate
sodium 2α-benzoyl-8β-hydroxy-2β,4,5,7,8,11αH-eudesman-12-oate
8β-hydroxy-4,7,8αH-eudesama-5,11(13)-dien-12-oic acid
8β-hydroxy-5,7,8,11αH-eudesam-4( 15)-en-12-oic acid
8β-hydroxy-4,5,7,8,11αH-eudesman-12-oic acid
2α,8β-dihydroxy-2β-4,5,7,8,11αH-eudesaman-12-oic acid
2α,8β-dihydroxy-4(15)11(13)-eudesamadien-12-oic acid
2α-benzoyl-8β-hydroxy-2β,4,5,7,8,11αH-eudesaman-12-oic acid
1-[2α-hydroxy-11,12-dihydro-5,7,8αH-eudesm-4(15)-en-8,12-olidyl]-pyrrolidine:

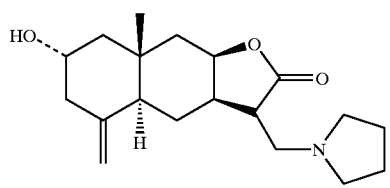

1-[2α-benzoyloxy-11,12-dihydro-5,7,8αH-eudesm-4(15)-en-8,12-olidyl]-pyrrolidine

Following synthesis, the compounds of the present invention can be isolated and purified by established methods to yield pharmaceutically acceptable material for administration to mammals.

The compounds for use in the methods of the present invention can be, and are preferably, administered as a medicament, i.e., a pharmaceutical composition. Preferred are oral and intraperitoneal dosage forms of the compounds.

The pharmaceutical compositions used in the methods of this invention for administration to animals and humans comprise the compound of the present invention in combination with a pharmaceutical carrier or excipient. The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian..

The compounds of the present invention can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include, without limitation, the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate, (e) agents for retarding dissolution, e.g., paraffin, (f) resorption accelerators, e.g., quaternary ammonium compounds; (g) surface active agents, e.g., cetyl alcohol, glycerol monostearate; (h) adsorptive carriers, e.g., kaolin and bentonite, (i) lubricants, e.g., talc, calcium and magnesium stearate and solid polyethylene glycols.

The tablets, dragees, capsules and pills comprising the active compound can have the customary coatings, envelopes and protective matrices, which can contain opacifiers. They can be so constituted that they release the active ingredient only or preferably in a particular part of the intestinal tract, possibly over a period of time. The coatings, envelopes and protective matrices can be made, for example, from polymeric substances or waxes. The compounds of the present invention can also be made up in microencapsulated form together with one or several of the above-mentioned diluents. The diluents to be used in pharmaceutical compositions adapted to be formed into suppositories can, for example, be the usual water-soluble diluents, such as polyethylene glycols and fats (e.g., cocoa oil and high esters, e.g., C14-alcohol with C16-fatty acid) or mixtures of these diluents.

The pharmaceutical compositions which are solutions and emulsions can, for example, contain the customary diluents, such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils, ground nut oil, glycerol, tetrahydrofurfuryl alcohol, polyethylene glycols and fatty acid esters of sorbitol or mixtures thereof For parental administration, solutions and suspensions should be sterile, e.g., water or arachis oil and, if appropriate, blood-isotonic. The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum metahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil), and sweetening agents, (e.g., saccharin and aspartame). The pharmaceutical compositions will generally contain from 0.5 to 90% of the active ingredient by weight of the total composition. In addition to the compounds of the present invention, the pharmaceutical compositions and medicaments can also contain other pharmaceutically active compounds. Any diluent in the medicaments of the present invention can be any of those mentioned above in relation to the pharmaceutical compositions. Such medicaments can include solvents of molecular weight less than 200 as the sole diluent. It is envisaged that the compounds of the present invention will be administered perorally, parenterally (for example, intramuscularly, intraperitoneally, subcutaneously, transdermally or intravenously), rectally or topically preferably orally or parenterally, especially perlingually, or intravenously.

The dosage rate, e.g., 0.5 to 500 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it can in some case suffice to use less than a minimum dosage rate, while other cases an upper limit must be exceeded to achieve the desired results. Where larger amounts are administered, it can be advisable to divide these into several individual administrations over the course of the day.

While not wishing to be bound by any particular theory, it is believed in one aspect that by inhibiting the activity of hormone-sensitive lipase, the compounds of the present invention intervene in the lipolysis of stored triglycerides and their metabolism into fatty acids and glycerol. As a metabolic sequella, elevated glucose levels can be reduced. The metabolism of fat provides three times as much caloric energy as do carbohydrates or proteins. As such, it is a fuel source whose utilization is limited only by its relative abundance. In the liver, free fatty acids undergo $\alpha$-oxidation, which consequently inhibits glycolysis by negative feedback mechanisms while simultaneously promoting gluconeogenesis. Additionally, the released glycerol is utilized as a three-carbon substrate in gluconeogenesis thus contributing to an increased level of hepatic glucose output. Under normal circumstances of metabolic regulation, enhanced lipolysis of stored triglycerides in adipose tissue occurs after prolonged periods of fasting, and is quickly suppressed following ingestion of a meal by the actions of insulin. However, in the insulin-resistant state of type II diabetes, this suppression of lipolysis by insulin is lost, even after eating. Under these conditions, the liver remains in a constant state of gluconeogenesis, and glucose transport into muscle tissue is reduced, resulting in overt hyperglycemia.

The anti-lipolytic effect of the compounds of the present invention in adipose tissue results in a reduction of plasma free fatty acids and glycerol concentrations. In turn, a reversal from gluconeogenesis to glycolysis in the liver can be achieved due to the decreased availability of fatty acids as a fuel source, with an eventual lowering of plasma glucose levels as the is once again reestablished as the primary energy source. Lowering of free fatty acids has an additional impact on the function of the pancreas. In the $\beta$-cell, elevations of free fatty acids cause an impairment in the insulin secretory mechanisms, as demonstrated by Unger (1995, Diabetes 44:863–870), with compounds demonstrating NEFA lowering properties preventing and restoring proper $\beta$-cell functioning. Thus, the compounds of the present invention thus achieve a lowering or normalization of elevated blood glucose and insulin levels, and amelioration of the insulin-resistant state of muscle in addition to their beneficial effect on circulating lipids.

Taken together, the results from the enzyme inhibition studies, the lipolysis assays and animal studies described herein suggest that the compounds of the present invention possess a unique mechanism of action, and are not expected to display the toxic cellular transformation effects observed with the prior art thiazolidinediones. They are thus highly useful and desirable therapeutic agents having utility in a variety of disease states where the lowering of blood glucose levels and/or the inhibition of lipolysis is necessary for the treatment of the patients. Such disease states include diabetes, and especially maturity-onset, or Type II diabetes, insulin resistance associated with dyslipidemia and normoglycemia referred to as Syndrome X, hypertension and atherosclerosis.

The enzyme hormone-sensitive lipase (HSL) is distinguished from other endogenous lipase enzyme systems in that its activity is governed by the action of various steroid and non-steroid hormones and secreted neurotransmitter substances via receptor-mediated second messenger pathways. Examples of such substances include insulin, corticosterone, and norepinephrine. The primary location of hormone-sensitive lipase is in adipose tissue, where it is involved in the coordinated regulation of lipid metabolism. As mentioned above, the activity of this enzyme is responsible for mobilization of stored triglycerides to provide fuel sources in times of fasting. Recent expression of the gene for mammalian hormone-sensitive lipase in a transfected bacterial vector has provided a means for the isolation of pure hormone-sensitive lipase protein. This has lead to the development of an in vitro assay for assessing direct effects of potential therapeutic agents on the activity of the enzyme itself without the encumbrances of other signaling and regulating entities found in a whole cell system.

An appropriate model for evaluating adipose cell function in tissue culture conditions is the transformed NIH-3T3 cell. Incubation of the 3T3 cell line with dexamethasone and 3-isobutyl-1-methylxanthine (IBMX) results in differentiation from a fibroblastic adipoblast into a mature adipocyte capable of performing insulin-regulated lipogenesis and norepinephrine-mediated lipolysis. As such, the inhibition of lipolytic activity can be assessed for potential agents in whole cell and permeabilized conditions. An assay of this type has been used to correlate the effects of potential therapeutic agents assessed in the purified enzyme system in an appropriate, intact biological circumstance.

Under normal metabolic regulatory control, the breakdown of stored triglyceride in the adipose tissue of mammals is tightly regulated by the hormone insulin. When insulin levels are high, such as after its release from the β-cell of the pancreas in response to high circulating blood levels of glucose, the activity of hormone-sensitive lipase is inhibited. As glucose levels decrease, the levels of insulin decrease in a parallel fashion. At some point during an extended fasting period, the levels of insulin are decreased below those required for inhibition of hormone-sensitive lipase. As a consequence, the catalytic activity of the enzyme is enhanced resulting in the release of non-esterified free fatty acids (NEFA), and glycerol from stored triglyceride reservoirs.

Normal, non-diabetic animals can thus be utilized for determination of hormone-sensitive lipase inhibition by administering test compounds prior to the initiation of a fasting period when insulin levels are high. A decrease in the level of plasma NEFA after an extended fasting period of 18 hrs would be indicative of inhibiting the mobilization of triglyceride depots from the adipose sites through the hormone-sensitive lipase pathway.

In Type II diabetes, the insulin regulatory mechanism for lipolysis does not function properly. Due to the state of insulin-resistance, and despite the elevation of insulin levels over the normal range in certain instances, the inhibition of hormone-sensitive lipase activity is severely diminished such that the lipolytic activity on stored triglycerides is enhanced, resulting in highly elevated fasting plasma NEFA levels. In addition, recent experimental evidence suggests that a transient state of insulin-resistance can be achieved in normal, non-diabetic individuals following the direct infusion of NEFA into the circulatory system. This data would support a pathological role for elevated plasma NEFA in Type II diabetes.

At the present time, the exact etiology for the development of adult-onset Type II diabetes is unknown. However, it is correlated with marked obesity since 70% of this patient population can be categorized as being obese under the general criterion set forth by American Diabetes Association, National Institutes of Health guidelines. As such, non-human mammals exhibiting a similar pathophysiological profiles serve as appropriate models for assessing the anti-dyslipidemic and anti-diabetic properties of potential pharmaceutical agents.

Animal models displaying these overall characteristics include the ob/ob and KK/Ay strains of mice, and the Zucker fa/fa (ZDF) rat. The ob/ob mouse begins to develop a diabetic profile at 4 weeks of age. Plasma glucose values increase up until 9–10 weeks, at which time the levels begin to plateau. In addition to being hyperglycemic, the ob/ob mouse displays elevated levels of NEFA, triglyceride production, and an insulin-resistant state. Furthermore, a parallel increase in plasma insulin levels occurs as a consequence of hyperglycemia. As plasma insulin levels peak, an improvement in hyperglycemia is seen. However, the amount of insulin present is not sufficient to completely normalize the insulin-resistant state during an oral glucose tolerance test.

Overall, the KK/Ay is similar to the ob/ob with some differences being noted. The onset of the Type II profile occurs much later, roughly 3–4 months of age, and persists for as long as 1 year. Both mouse models display hyperinsulinemia, hyperglycemia, insulin-resistance and dyslipidemia similar to that seen in the clinical setting.

The ZDF rat is also similar to the ob/ob and KK/Ay mouse in that all the general attributes of the Type II-like profile with one added exception. In contrast to the mouse models, which exhibit severe hyperinsulinemia, the ZDF rat displays a progressive decline in the ability to secrete insulin from the α-cell beginning at 10 weeks of age, resulting in a state of hypoinsulinemia. As such, this condition is similar in profile to a subtype of Type II diabetic patients which fail to respond to certain classes of pharmacological agents, such as the sulfonylureas, and can require insulin therapy.

The present invention can be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Preparation of Intermediates and Compounds

Isolation and Purification of 2α-hydroxy-5,7,8αH-eudesm-4(15),11(13)-dien-8,12-olide This compound is used as an intermediate in the preparation of several of the compounds of the present invention. 2α-hydroxy-5,7,8αH-eudesm-4(15),11(13)-dien-8,12-olide was isolated from Iva microcephala Nutt by a modification of the method reported by Herz et al., *J. Org. Chem.*, 27:905–910, 1962. The flower heads, leaves, and tender stems of plants were dried, ground, and extracted in Soxhlet extractor with a mixture of petroleum ether and ether (2:1 v/v) with stirring for 5 hrs. The crude 2-hydroxy-5,7,8α-eudesm-4(15),11(13)-dien-8,12-olide started precipitating out in 2 hrs. The extract was allowed to cool at room temperature overnight, and then filtered, washed with the same mixture of solvent to obtain crude 2-hydroxy-5,7,8α-eudesm-4(15),11(13)-dien-8,12-olide (2.93% yield). The crude 2-hydroxy-5,7,8α-eudesm-4(15),11(13)-dien-8,12-olide was crystallized from a mixture of CH2Cl2, ether, and petroleum ether to obtain 2-hydroxy-5,7,8α-eudesm-4(15), 11(13)-dien-8,12-olide, m.p. 127–129° C., 2.86% yield. 1H-NMR (CDCl$_3$, 400 MHZ) d 6.13 (1H, d, H-13α), 5.59 (1H, d, H-13α), 4.87 (1H, d, H-15α), 4.54 (1H, d, H-15α), 4.49 (1H, ddd, H-8α), 3.82 (1H, m, H-2α), 2.98 (1H, ddd, H-7α), 1.88 (1H, dd, H-5α), and 0.82 (1H, s, C10-CH3). 13C-NMR (CDCl$_3$, 100 MHZ) d 170.5 (C-12), 145.9 (C-4), 141.9 (C-11), 120.5 (C-13), 109.3 (C-15), 76.6 (C-8), 67.1 (C-2), 50.9 (C-5), 46.3 (C-7), 45.5 (C-9), 41.1 (C-1), 40.5 (C-3), 34.0 (C-10), 27.3 (C-6), and 18.7 (C-14).

Preparation of 2α-benzoyloxy-5,7,8αH-eudesma-4(15),11(13)-dien-8,12-olide

The following reaction scheme was used:

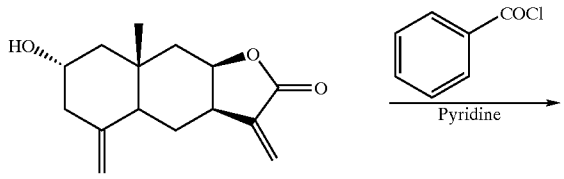

2α-hydroxy-5,7,8αH-eudesma-4(15),11(13)-dien-8,12-olide

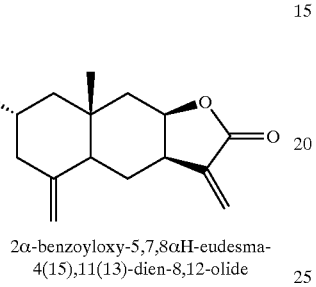

2α-benzoyloxy-5,7,8αH-eudesma-4(15),11(13)-dien-8,12-olide

2α-Hydroxy-eudesma-4(15),11(13)-dien-8,12-olide (4.0 g 16.1 mmole) was dissolved in $CH_2Cl_2$ (13 ml) and added excess benzoyl chloride (4.0 g, 28.4 mmole) and pyridine (3.1 ml) with stirring at 0° C. for 2 hrs. and then continued stirring at room temperature for overnight. The reaction mixture was poured into ice water with stirring. The precipitate was collected by filtration and washed with ice water. The solid was dissolved in $CH_2Cl_2$ (30 ml) and dried over anhydrous $Na_2SO_4$. The $CH_2Cl_2$ solution was evaporated in vacuo to give the crude product (7.0 g), which was purified by Silica gel column chromatography eluted with $CH_2Cl_2$ and 1% MeOH-$CH_2Cl_2$ successively. The product (5.08 g) was crystallized from a mixture of $CH_2Cl_2$, ether, and petroleum ether to obtain 2α-benzoyloxy-5,7,8αH-eudesma-4(15),11(13)-dien-8,12-olide (4.5 g, 79.3%) m.p. 127–129° C. Estimated purity 99.9% by HPLC. $^1$H-NMR (CDCl3, 400 MHZ) δ7.99 (2H, d, H-2",6"), 7.55 (1H, dd, H-4"), 7.43 (2H, dd, H-3",5"), 6.14 (1H, d, H-13-α), 5.61 (1H,d, H-13α), 5.13 (1H, m, H-2β), 4.97 (1H, d, H-15β), 4.63 (1H, d, H-15α), 4.51(1H, ddd, H-8α), 3.00 (1H, ddd, H-7α), 2.05 (1H, dd, H-5α), and 0.94 (3H, s, $C_{10}$-$CH_3$). $^{13}$C-NMR (CDCl$_3$, 100 MHZ) δ170.1 (C-12), 165.8 (C-1'), 144.9 (C-4), 141.8 (C-11), 132.9 (C-1"), 130.5 (C-4"), 129.6 (C-2",6"), 128.4 (C-3",5"), 120.5 (C-13), 110.4 (C-15), 76.4 (C-8), 70.3 (C-2), 46.9 (C-5), 45.7 (C-7), 44.9 (C-9), 40.9 (C-1), 40.5 (C-3), 34.2 (C-10), 27.2 (C-6), and 18.5 (C-14). Anal. Calcd. for $C_{22}H_{24}O_4$, C% 74.90%, H 6.81%. Found C% 75.06%, H% 6.95%.

Preparation of 2α-hydroxy-4,5,7,8,11αH-eudesman-8,12-olide

2α-hydroxy-4,5,7,8,11αH-eudesman-8,12-olide was used as an intermediate in the preparation of certain compounds of the present invention. A solution of 2α-hydroxy-5,7,8αH-eudesma-4(15),11(13)-dien-8,12-olide (4.0 g) in methanol (150 ml.) containing acetic acid (1.5 ml.) was added platinum oxide (0.12 g). The reaction mixture was hydrogenated on a Parr shaker at 40 psi at room temperature for 17 hrs. The reaction mixture was filtered and concentrated in vacuo. The residue was washed with ice water to get a white powder product, 2α hydroxy-4,5,7,8,11αH-eudesman-8,12-olide (3.36 g, 82.7%); m.p. 154–155° C. 1H-NMR (CDCl$_3$, 400 MHZ) δ4.42 (1H, ddd, H-8α), 3.97 (1H, m, H-2α), 2.40 (1H, m, H-4α), 2.1 (1H, dd, H-7α), 1.17 (3H, d, $C_{11}$-$CH_3$), 1.01 (3H, s, $C_{10}$-$CH_3$), and 0.91 (3H, d, $C_4$-$CH_3$). $^{13}$C-NMR (CDCl$_3$, 100 MHZ) δ179.5 (C-12), 78.0 (C-8), 63.6 (C-2), 51.1 (C-5), 45.0 (C-7), 43.5 (C-11), 42.9 (C-9), 41.6 (C-1), 41.4 (C-4), 34.5 (C-3), 34.2 (C-10), 23.8 (C-6), 22.1 (C-14), 15.6 (C-15) and 9.3 (C-13).

Preparation of 2α-benzoyloxy-4,5,7,8,11αH-eudesman-8,12-olide

2αBenzoyloxy-4,5,7,8,11αH-eudesman-8,12-olide was prepared in accordance with the following reaction scheme:

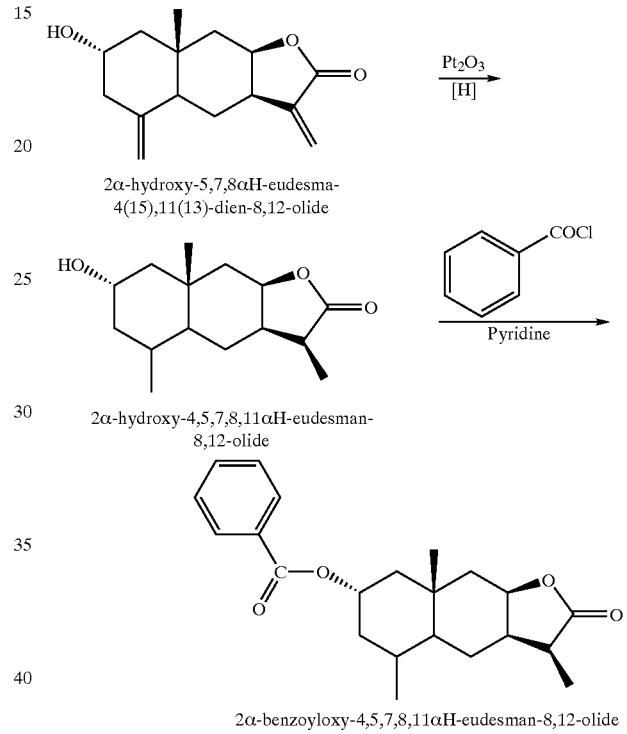

2α-hydroxy-5,7,8αH-eudesma-4(15),11(13)-dien-8,12-olide

2α-hydroxy-4,5,7,8,11αH-eudesman-8,12-olide

2α-benzoyloxy-4,5,7,8,11αH-eudesman-8,12-olide

2α-hydroxy-4,5,7,8,11αH-eudesman-8,12-olide (3.36 g, 13.3 mmole) was dissolved in $CH_2Cl_2$ (15 ml.) and added excess benzoyl chloride (4.0 g, 28.4 mmole) and pyridine (7.6 ml) with stirring at 0° C. for 2 hrs. and then continued stirring at room temperature for overnight. The reaction solution was evaporated and poured into ice water (700 ml) with stirring. The precipitate was collected by filtration and washed with ice water. The solid was dissolved in $CH_2Cl_2$ (50 ml) and dried over anhydrous $Na_2SO_4$. The $CH_2Cl_2$ solution was evaporated in vacuo to obtain crude product, 7.51 g, The product was purified by Silica gel column chromatography ($CH_2Cl_2$ as eluent). The product was recrystallized from mixtures of $CH_2Cl_2$, ether, and petroleum ether to obtain pure 2α-benzoyloxy-4,5,7,8,11αH-eudesman-8,12-olide (3.38 g, 70.8%), m.p. 181–183° C. Estimated purity 99.1% by HPLC. $^1$H-NMR (CDCl$_3$, 400MHz) δ8.00 (2H, d, H-2",6"), 7.53 (1H, dd, H-4"), 7.41 (2H, dd, H-3",5"), 5.32 (1H, m, H-2β), 4.44 (1H, ddd, H-8α), 2.04 (1H, dd, H-7α), 1.16 (3H, d, $C_{11}$-$CH_3$), 1.10 (3H, s, $C_{10}$-$CH_3$), 0.99 (3H, d, $C_4$-$CH_3$). $^{13}$C-NMR (CDCl3, 100 MHz) δ179.4 (C-12), 166.1 (C-1'), 132.8 (C-1"), 130.7 (C-4"), 129.5 (C-2",6"), 128.3 (C-3",5"), 77.6 (C-8), 68.0 (C-2), 47.1 (C-5), 44.9 (C-9), 43.7 (C-7), 41.5 (C-1), 41.3 (C-4), 39.1 (C-11), 34.5 (C-3), 34.0 (C-10), 23.8 (C-6), 21.9

(C-14), 15.5 (C-15), and 9.3 (C-13). Anal. Calcd. for C22H28O4, C% 74.15%, H% 7.86. Found C% 74.17%, H% 8.00%.

The compound 2α-acetoxy-4,5,7,8,11αH-eudesman-8,12-olide was prepared following a procedure as above.

Preparation of 2α-cyclopropanoyloxy-5,7,8,11αH-eudesm-4(15)-en-8,12-olide and 2α-benzoyloxy-5,7,8,11αH-eudesm-4(15)-en-8,12-olide These compounds were prepared from 2α-hydroxy-5,7,8,11αH-eudesm-4(15)-en-8,12-olide using cyclopropanecarbonyl chloride and benzoyl chloride, respectively, in accordance with the procedure described herein for the preparation of 2α-benzoyloxy-5,7,8αH-eudesma-4(15),11(13)-dien-8,12-olide.

Isolation and Purification of 5,7,8αH-eudesma-4(15),11(13)-dien-8,12-olide; 4,7,8αH-eudesma-5(6),11(13)-dien-8,12-olide; and 5,7,8,11αH-eudesm-4(15)-en-8,12-olide A commercial source of crude 5,7,8αH-eudesma-4(15),11(13)-dien-8,12-olide, isohelenin (Sigma, Cat. 1-1639, purity 80%) was obtained. To purify 5,7,8αH-eudesma-4(15),11(13)-dien-8,12-olide, the material (20.0 g) was applied to a silica gel column chromatography with petroleum ether containing increasing amounts of ether as eluent to give 60 fractions each of 100–150 ml. The fractions were combined, based on TLC similarities, to yield three major fractions and further purified by re-chromatography on silica gel column with the same eluents. The fraction 2-4 contained 4,7,8αH-eudesma-5(6),11(13)-dien-8,12-olide (20.6%), faction 11-19 contained 5,7,8αH-eudesma-4(15),11(13)-dien-8,12-olide (57.5%), and fraction 41-51 contained 5,7,8,11αH-eudesma-4(15)-en-8,12-olide (13.0%). The structures of these compounds were elucidated by mass spectroscopy, and high field NMR including 2D NMR studies.

4,7,8αH-Eudesma-5(6),11(13)-dien-8,12-olide

Prisms (from a mixture of $CH_2Cl_2$, $Et_2O$, and petroleum ether), m.p. 73–75° C. Estimated purity 99.8% by HPLC (Condition: Column-Dynamax C-18, Detector-UV 203/210 nm, Flow rate-1.6 ml/min, Mobile phase-65% acetonitrile). $^1$H-NMR ($CDCl_3$, 400 MHz): δ6.15 (1H, d, H-13β), 5.59 (1H, d, H-13α), 5.12 (1H, dd, H-6α), 4.78 (1H, ddd, H-8α), 3.55 (1H, dd, H-7α), 2.41 (1H, m, H-4α), 2.08(1H, dd, H-9β), 1.53 (1H, dd, H-9α), 1.16(3H, s, $C_{10}$-$CH_3$), and 1.06 (3H, d, $C_4$-$CH_3$) $^{13}$C-NMR ($CDCl_3$, 100 MHZ): δ170.06 (C-12), 149.15 (C-11), 139.91 (C-5), 121.74 (C-13), 118.85 (C-6), 76.52 (C-8), 42.75 (C-7), 41.81 (C-9), 39.58 (C-1), 37.68 (C-4), 32.80 (C-3), 32.75 (C-10), 28.66 (C-2), 22.63 (C-14), and 16.84 (C-15).

5,7,8αH-Eudesma-4(15), 11(13)-dien-8,12olide

Needles (from a mixture of $CH_2Cl_2$, $Et_2O$, and petroleum ether). m.p. 108–110° C. Estimated purity 99.8% by HPLC (Condition: Column-Dynamax C-18, Detector-UV 203/210 nm, Flow rate-1.6 m/min, Mobile phase-65% ACN). EIMS m/z 232 [M]+(21), 217 (17), 190 (60), 176 (18), 164 (19), 161 (8), 145 (20), 131 (27), 121 (40), 107 (32), 105 (42), 93(70), 91 (77), 79 (100), 67 (76), and 53 (97). $^1$H-NMR ($CDCl_3$, 400 MHZ): δ6.11 (1H, d, H-13β), 5.57 (1H, d, H-13α), 4.75 (1H, d, H-15β), 4.48 (1H, ddd, H-8α), 4.42 (1H, d, H-15α), 2.95 (1H, ddd, H-7α), 2.16 (1H, dd, H-9β), 1.82 (1H, dd, H-5α), 1.37 (1H, dd, H-9α), 1.55 (1H, dd, H-6α), 1.21 (1H, ddd, H-6β) and 0.81 s, C10-CH3???13C-NMR (CDCl3, 100 MHZ): δ170.71 (C-12), 149.03 (C-4), 142.28 (C-11), 120.12 (C-13), 106.68 (C-15), 76.90 (C-8), 46.28 (C-5), 42.26 (C-7), 41.44 (C-9), 40.61 (C-1), 36.89 (C-3), 34.36 (C-10), 27.55 (C-6), 22.76 (C-2), and 17.74 (C-14).

5,7,8,11αH-Eudesma-4(15)-en-8,12-olide

Needles (from a mixture of CH2Cl2, Et2O, and petroleum ether). m.p. 171–173° C. Estimated purity 99.4% by HPLC (Condition: Column-Dynamax C-18, Detector-UV 203/210 nm, Flow rate-1.6 ml/min, Mobile phase-65% ACN). $^1$H-NMR (CDCl3, 400 MHZ): δ4.76 (1H, d, H-15β), 4.47 (1H, d, H-15α), 4.46 (1H, ddd, H-8α), 2.79 (1H, dq, H-11α), 2.33 (1H, ddd, H-7α), 2.15 (1H, dd, H-9β), 1.76 (1H, dd, H-5α), 1.56 (1H, dd, H-6α), 1.45 (1H, dd, H-9α), 1.21 (3H, d, $C_{11}$-$CH_3$), 1.12 (1H, ddd, H-6β), and 0.79 (3H, s, $C_{10}$-$CH_3$). $^{13}$C-NMR (CDCl3, 100 MHZ): δ170.90 (C-12), 149.49 (C-4), 106.48 (C-15), 77.92 (C-8), 46.62 (C-5), 42.33 (C-7), 41.85 (C-9), 41.68 (C-11), 40.41 (C-1), 36.86 (C-3), 34.92 (C-10), 22.77 (C-2), 21.35 (C-6), 17.86 (C-14, and 9.36 (C-13).

Preparation of 4,5,7,8,11 αH-eudesman-8,12-olide

A solution of 5,7,8αH-eudesma-4(15),11(13)-dien-8,12-olide (5.0 g, 0.021 mole) in methanol (135 ml) containing acetic acid (1.0 ml) was added platinum (IV) oxide (0.12 g). The reaction mixture was hydrogenated at 40 psi at room temperature for overnight. The reaction mixture was filtered and evaporated in vacuo. The residue was dissolved in methylene chloride (100 ml.) and dried over anhydrous sodium sulfate. The methylene chloride solution was evaporated to obtain crude product, 4.95 g. The product was recrystallized from a mixture of methylene chloride and petroleum ether to yield 4.52 g 4,5,7,8,11αH-eudesman-8,12-olide, m.p. 144–146° C., 88.9% yield. $^1$H NMR ($CDCl_3$, 400 MHz) δ4.42 (1H, ddd, H-8α), 2.74 (1H, m, H-4α), 2.36 (1H, m, H-7α), 1.17(3H, d, $C_{11}$-$CH_3$), 0.96 (3H, s, $C_{10}$-$CH_3$), and 0.86 (3H, d, $C_4$-$CH_3$). $^{13}$C NMR (CDCl3, 100 MHz) δ179.7 (C-12), 78.4 (C-8), 45.3 (C-5), 44.2 (C-7), 42.3 (C-9), 41.7 (C-1), 41.4 (C-11), 33.7 (C-4), 33.3 (C-3), 33.1 (C-10), 24.6 (C-2), 21.1 (C-6), 16.8 (C-14), 15.0 (C-15), and 9.3 (C-13).

EXAMPLE 2A

Additional Compounds

In an analogous manner to that described in Example 1 above, the following additional compounds were prepared:

2α-acetoxy-5,7,8αH-eudesma-4(15),11(13)-dien-8,12-olide, m.p. 125–127° C.

2α-isobutyryloxy-5,7,8αH-eudesma-4(15),11(13)-dien-8,12-olide, m.p. 76–78° C.

2α-propanoyloxy-5,7,8αH-eudesma-4(15),11(13)-dien-8,12-olide, m.p. 98–100° C.

2α-furoyloxy-5,7,8αH-eudesma-4(15),11(13)-dien-8,12-olide, m.p. 98–100° C.

2α-cyclopropanoyloxy-5,7,8αH-eudesma-4(15),11(13)-dien-8,12-olide, m.p. 160–163° C.

2α-acetoxy-4,5,7,8,11αH-eudesman-8,12-olide, m.p. 183–185° C.

2α-cyclopropanoyloxy-5,7,8,11αH-eudesm-4(15)-en-8,12-olide, m.p. 157–160° C.

2α-benzoyloxy-5,7,8,11αH-eudesm-4(15)-en-8,12-olide, m.p. 150–153° C.

EXAMPLE 2B

Further Examles

Preparation of 1-[2α-hydroxy-11,12-dihydro-5,7,8αH-eudesm-4(15)-en-8,12olidyl]-pyrrolidine 1-[2α-hydroxy-11,12-dihydro-5,7,8αH-eudesm-4(15)-en-8,12-olidyl]-pyrrolidine was synthesized using the Michael addition methodology described in Hejchman et al. (1995, 38: 3407–3410). Ivalin (2α-hydroxy-4(15),11(13) eudesmadien-12,8-olide) (1.5 mmol) was dissolved in THF (5 ml). The solution was cooled in the freezer for 15 minutes. Pyrrolidine (3 mmol) in THF (5 ml) was added to the solution of invalin. The mixture was kept in the refrigerator at 5° C. for 20 hours. The solvent was evaporated. The residue was dissolved in ether and filtered through silica gel pad. The solvent was evaporated and the residue kept in vacuo for 24 hours to remove traces of pyrrolidine. The product was crystallized from a mixture of ethyl acetate and hexane in about 55% yield, mp 121–124° C.

In the same way, 1-[11,12-dihydro-5,7,8αH-eudesm-4(15)-en-8,12-olidyl]-pyrrolidine was synthesized from isohelenin (5,7,8αH-eudesma-4(15),11(13)-dien-8,12-olide); and 1-[2α-benzoyloxy-11,12-dihydro-5,7,8αH-eudesm-4(15)-en-8,12-olidyl]-pyrrolidine was synthesized from 2α-benzoyloxy-5,7,8αH-eudesma-4(15),11(13)-dien-8,12-olide.

EXAMPLE 2C

Further Examples

Preparation of Open-Ring Structures

The starting compound (8 moles) was added to a solution of NaOH (8 moles) in 90% EtOH (10 to 20 mls, as required), and the mixture stirred at 60–90° C. for 2 to 3 hours:

| Starting Compound | Product |
|---|---|
| 4,5,7,8,11αH-eudesman-8,12-olide | 8β-hydroxy-4,5,7,8,11αH-eudesman-12-oic acid |
| 5,7,8αH-eudesma-4(15),11(13)-dien-8,12-olide | 8β-hydroxy-5,7,8αH-eudesma-4(15),11(13)-dien-12-oic acid |
| 4,7,8αH-eudesma-5(6),11(13)-dien-8,12-olide | 8β-hydroxy-4,7,8αH-eudesama-5(6),11(13)-dien-12-oic acid |
| 5,7,8,11αH-eudesm-4(15)-en-8,12-olide | 8β-hydroxy-5,7,8,11αH-eudesam-4(15)-en-12-oic acid |
| 2α-hydroxy-4,5,7,8,11αH-eudesman-8,12-olide | 2α,8β-dihydroxy-2β-4,5,7,8,11αH-eudesaman-12-oic acid |
| 2α-hydroxy-5,7,8αH-eudesm-4(15),11(13)-dien-8,12-olide | 2α,8β-dihydroxy-4(15)11(13)-eudesamadien-12-oic acid |
| 2α-benzoyloxy-4,5,7,8,11αH-eudesman-8,12-olide | 2α-benzoyl-8β-hydroxy-2β,4,5,7,8,11αH-eudesaman-12-oic acid |

The solvent was evaporated at reduced pressure, and the product carboxylate salt recrystallized from $CH_3CN$ and EtOH or MeOH and ethyl acetate.

EXAMPLE 3

Dosage Form

The compounds of the present invention can be formulated for oral pharmaceutical administration to a patient in need of blood glucose lowering as follows:

| Component | mg/tablet |
|---|---|
| Compound of the invention | 50 |
| starch | 50 |
| mannitol | 75 |
| magnesium stearate | 2 |
| stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32 inch punch with a hardness of 4 kg. These tablets will disintegrate within a half hour according to the method described in USP XVI.

EXAMPLE 4

Hormone-Sensitive Lipase

Potential to directly inhibit the activity of hormone-sensitive lipase is determined in an in vitro purified enzyme system. Recombinant hormone-sensitive lipase protein isolated from a bacterial expression vector was pre-incubated with a compound of the invention (e.g., 100 $\mu$M) prior to the addition of substrate, emulsified triolein phosphatidylcholine/phosphatidylinositol (PC/PI), to initiate the reaction. At various time points, aliquots of the reaction were taken, and the level of glycerol used as an index of enzyme activity. Pharmacological specificity is determined by incubating test compound with other mammalian and non-mammalian lipase enzyme systems to assess inhibition of activity. The assay was conducted using triolein concentrations from 42 $\mu$M to 835 $\mu$M.

EXAMPLE 5

Inhibition of Hormone Sensitive Lipase

In a similar manner to that described in Example 4 above, 2α-benzoyloxy-5,7,8αH-eudesma-4(15),11(13)-dien-8,12-olide at 100 $\mu$M was evaluated for ability to inhibit the activity of hormone-sensitive lipase on cholesterol oleate PC/PI. The assay was conducted as using cholesterol oleate concentrations from 12.5 $\mu$M to 225 $\mu$M.

EXAMPLE 6

Hormone Sensitive Lipase and 3T3-L1 Hormone Sensitive Lipase

In a similar manner to that described in Example 4 above, 2α-benzoyloxy-4,5,7,8,11αH-eudesman-8,12-olide at 100 $\mu$M was evaluated for ability to inhibit the activity of recombinant hormone-sensitive lipase and hormone-sensitive lipase derived from a preparation of 3T3-cell lysate on glycerol-stabilized triolein. The results are show in Table 1.

TABLE 1

| Triolein Concentration ($\mu$M) | % inhibition Purified HSL | 3T3-L1 lysate |
|---|---|---|
| 30 | 77 | 63 |
| 67 | 78 | 56 |
| 100 | 82 | 51 |
| 201 | 64 | 41 |
| 400 | 50 | 38 |
| 601 | 40 | 30 |
| 800 | 18 | 18 |
| 1000 | 27 | 15 |

EXAMPLE 7
Further Enzyme Evaluations

To demonstrate that the specificity of the compounds of the present invention toward hormone sensitive lipase, 2α-benzoyloxy-5,7,8αH-eudesma-4(15),11(13)-dien-8,12-olide was evaluated for inhibition of Candida rugosa lipase toward emulsified Triolein substrate PC/PI. As shown in Table 2 below, 2α-benzoyloxy-5,7,8αH-eudesma-4(15),11 (13)-dien-8,12-olide did not inhibit enzyme activity.

TABLE 2

| Triolein Substrate, $\mu$M | Candida Lipase (DMSO) | sem | Candida Lipase + test compound | sem | % Inhibition |
|---|---|---|---|---|---|
| 42 | 5.40 | 0.44 | 3.21 | 0.12 | 40 |
| 83.5 | 9.66 | 0.51 | 11.59 | 0.59 | -12% |
| 167 | 14.98 | 0.05 | 14.14 | 0.65 | 6.3 |
| 334 | 25.19 | 0.12 | 22.68 | 0.75 | 3.6 |
| 501 | 59.12 | 1.56 | 60.13 | 2.85 | -1.7 |
| 668 | 91.67 | 14.97 | 93.59 | 11.56 | -1.1 |
| 835 | 94.13 | 2.12 | 89.71 | 1.98 | 1.0 |

EXAMPLE 8
Further Enzyme Evaluations

The specificity of the compounds of the present invention was further demonstrated by evaluating inhibition of hepatic lipase and lipoprotein lipase, catalyzed by hydrolysis of glycerol stabilized Triolein substrate by 2α-benzoyloxy-4, 5,7,8,11αH-eudesman-8,12-olide at a concentration of 100 $\mu$M. The results are shown in Table 3.

TABLE 3

| Triolein Substrate, $\mu$M | Pur. Hepatic Lipase (DMSO) | Sem | +test compound | sem | Lipoprotein Lipase (DMSO) | sem | +test compound | sem |
|---|---|---|---|---|---|---|---|---|
| 30 | 0.11 | 0.02 | 0.08 | 0.03 | 0.6 | 0.1 | 0.7 | 0.1 |
| 67 | 0.20 | 0.03 | 0.37 | 0.08 | 1.7 | 1.7 | 1.8 | 0.2 |
| 100 | 1.35 | 0.17 | 0.69 | 0.05 | — | — | — | — |
| 134 | — | — | — | — | 4.8 | 4.8 | 4.9 | 0.3 |
| 201 | 6.11 | 0.14 | 6.36 | 0.20 | — | — | — | — |
| 264 | — | — | — | — | 9.6 | 9.6 | 10.3 | 0.8 |
| 400 | 29.20 | 3.20 | 30.80 | 3.06 | — | — | — | — |
| 1000 | 134.60 | 2.60 | 151.60 | 2.09 | 65.2 | 65.2 | 67.4 | 1.2 |

As can be seen in Table 5, compound 2α-benzoyloxy-4,5, 7,8,11αH-eudesman-8,12-olide failed to significantly inhibit the activities of the two enzymes evaluated.

EXAMPLE 9
Effect of the Compounds of the Present Invention on Lipolysis

Any in vitro assay for lipolysis was developed using 3T3-L1 cells. In this assay protocol, the 3T3-L1 adipocytes were permeabilized with digitonin and preincubated with the compounds of the present invention. Following this, the hormone sensitive lipase was activated with cAMP, which resulted in the hydrolysis of triglycerides to free fatty acids and glycerol. The liberated glycerol in the supernatant is quantified by a fluorescent assay performed in Microfluor B flat bottom plates.

The protocol for this lipolysis assay is as follows: 3T3-L1 adipocytes are used 14 days after differentiation is initiated. The media is carefully removed from the adipocytes. The cells are then gently washed twice with 300 $\mu$l of PBS. The cells are incubated with 0.2 ml of a permeabilization buffer consisting of 10 mM sodium phosphate, 150 mM sodium chloride, pH 7.4, 1% fatty-acid-free BSA, and digitonin (10 mg/ml). After 30 minutes incubation at 37 C., an additional 0.2 ml of permeabilization buffer containing the test compound was added and the cells were incubated for an additional 30 minutes. The buffer is then removed completely and replaced with 200 $\mu$l of permeabilization buffer containing test compounds and 200 $\mu$l of permeabilization buffer containing $N^6$-benzoyloxy-cAMP (0.6 mM), 8-thimethyl-cAMP (0.6 mM), 2 mM ATP and 4 mM $MgCl_2$. The cAMP is added to activate the cAMP-dependent protein kinase which in turn phosphorylates and activates the hormone sensitive lipase. The cells ar then incubated for 30 or 60 minutes at 37° C. A 350 $\mu$l aliquot of the buffer is removed and mixed with 100 ul of a 10% charcoal solution. The suspension is centrifuged (3000 RPM, 20 minutes) and 50 $\mu$l of the supernatant transferred to a 96 well flat bottom plate (Microfluor B) and frozen at −20° C. until assayed for glycerol by the following procedure.

Glycerol Assay: The amount of glycerol produced during lipolysis is measured by following two step reaction.

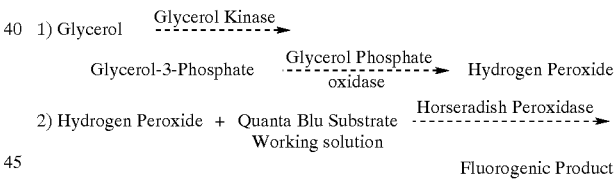

The reaction bufer consists of Kinase Buffer, pH 7.0 (2 mM MgCl2, 100 mM Triethanolamine, 2 mg/ml fatty acid free BSA), 130 µM ATP, 2 units/ml Glycerol kinase and 1 unit/ml glycerol phosphate oxidase. In the first step of the reaction, 50 ul of reaction buffer is added to 50 ul of supernatant from the lipolysis assay. A standard curve ranging from 0–12,000 pmoles is generated with standard glycerol diluted in permeabilization buffer. The plates are sealed and incubated at 37° C. for 30 minutes. The reaction results in conversion of glycerol to dihydroxyacetone phosphate and hydrogen peroxide.

In the second step of reaction, the hydrogen peroxide released is estimated using Quanta Blu flurorgenic substrate (Pierce, Rockford, Ill.) and HRP. 50 µl of Quanta Blu Working solution is added to the samples and standards followed by the addition of 50 ul of 250 units/ml HRP. The Quanta Blu Working solution is made by mixing 9 parts Quanta Blu substrate solution (Pierce, Quanta Blu Fluororgenic Peroxidase substrate kit, cat. #15169) and 1 part Kinase buffer (2 mM MgCl2, 100 mM Triethanolamine, 2 mg/ml fatty acid free BSA), pH 7.0. The plates are sealed and incubated at 37° C. for 30 minutes. The reaction is stopped by adding 50 ul / well Quanta Blu Stop solution (Pierce, Quanta Blu Fluorogenic Peroxidase Kit. Cat. #15169). The relative fluorescence units (RFU's) of the product are measured at an excitation and emission of 320 nm and 405 nm respectively, and corrected for background fluorescence. The final data is expressed as percent inhibition of lipolysis. In the calculation, cAMP stimulation of lipolysis is considered as 100% stimulation, or conversely as 0% inhibition. The final data is expressed as a percent inhibition calculated as follows.

$$\left[\frac{1-(RFU-neg\ cntrl\ RFU)}{pos\ cntrl\ RFU-neg\ cntrl\ RFU}\right] \times 100\%$$

RFU values are corrected, i.e., background subtracted.

EXAMPLE 10
Circulating Free Fatty Acid Levels in Overnight-fasted Normal Mice Male, C57/B16J lean mice were purchased from Jackson Laboratories, Bar Harbor, Me. Animals were housed and maintained in accordance with NIH guidelines and had free access to water and food ad libitum. Test compounds of the present invention were suspended in 0.25% methylcellulose (w/v in distilled water) and stored at −20° C. in single use aliquots. Animals received a daily dose via the intraperitoneal route of administration for 2 weeks. After the last dose, animals were fasted overnight. On the following morning, a 250 µl blood sample was drawn via the retro-orbital sinus into a tube containing an EDTA-saline solution and centrifuged at 1,200×g for 15 min. The plasma fraction was analyzed for non-esterified free fatty acid content (NEFA) using the NEFA C diagnostic kit (WAKO Chemicals USA, Richmond, Va.), and glycerol with the triglyceride GPO-Trinder diagnostic kit (Sigma) modified for use on a BM Hitachi 911 clinical chemistry analyzer. P-values from a student's t-test were calculated using the Prizm software data analysis program (Graphpad, Sorrento Calif.). The data is shown in Table 4, below. As can be seen, treatment of animals with a 2α-benzoyloxy-5,7,8αH-eudesma-4(15),11 (13)-dien-8,12-olide at a dose of 50 mg/kg resulted in a 27% reduction in fasting NEFA plasma levels.

TABLE 4

| Group | NEFA, mM | Glycerol, mg/dl | % reduction NEFA |
| --- | --- | --- | --- |
| Vehicle | 1.108 ± 0.193 | 36 | 0 |
| 2α-benzoyloxy-5,7,8αH-eudesma-4(15),11(13)-dien-8,12-olide, 50 mg/kg | 0.808 ± 0.080[a] | 28[b] | 27 |

[a]= p < 0.0055 compared to vehicle
[b]= p < 0.05 compared to vehicle

EXAMPLE 11
Effects in Fasted KK/Ay Mice

Male, KK/Ay mice were purchased from Clea Japan USA, Pennington, N.J. At 4 months of age, animals received daily intraperitoneal administration of 2α-benzoyloxy-5,7,8αH-eudesma-4(15),11(13)-dien-8,12-olide for 2 weeks. As described in Example 10, fasting plasma NEFA values were obtained. In addition, cholesterol and triglycerides were measured using BM reagent assay kits on a BM Hitachi 911 clinical chemistry analyzer. The data demonstrate significant reductions in NEFA, triglycerides, cholesterol and glycerol in mice receiving a 2α-benzoyloxy-5,7,8αH-eudesma-4 (15),11(13)-dien-8,12-olide. Plasma glucose levels were measured using a Boehringer Mannheim reagent assay kits on a Boehringer Mannheim Hitachi 911 clinical chemistry analyzer. Control mice showed a fasting plasma glucose level of 184±24 mg/dL, whereas animals dosed with the test compound showed a plasma glucose level of 90±29 mg/dL (p<0.01).

EXAMPLE 12
Effects in Fasted ob/ob Mice

Male, C57/B16J ob/ob mice were purchased from Jackson Laboratories (Bar Harbor, Me.). At 8–9 weeks of age, animals received daily compound administration via the intraperitoneal route of injection for a 2 week period at the indicated doses. Test compounds of the present invention were prepared as previously described in Example 10. At either 2 or 4 weeks of treatment, animals were fasted overnight and plasma NEFA levels determined as described in Example 11. The data are expressed as a percent reduction compared to animals that received vehicle alone. The test compounds elicited reductions in NEFA levels in treated animals. Glucose levels were measured using a Johnson & Johnson One-Touch Glucometer from a 20 µl blood sampled collected via the retro-orbital sinus with a heparinized micro-capillary tube. Fasting glucose values for the vehicle groups ranged between 250–350 mg/Dl compared to 100–120 mg/Dl for normal, non-diabetic mice. The data are expressed as a percent normalization using the following algorithm:

range=vehicle control value−normal value　　a).

% normalization=(vehicle control value−compound treated value)/range.　　b).

EXAMPLE 13
Effect on Circulating Free Fatty Acid Levels in Fasted ZDF Rats

Similar studies were conducted in the male, ZDF rat model of type II diabetes obtained from Genetic Models, Inc. (Indianapolis, Ind.). Animals received daily intraperitoneal doses of compounds as previously described. Plasma NEFA levels were obtained in the fasting state after 6 weeks of treatment. In the ZDF rat, a similar effect on lowering fasting NEFA levels occurred, as was seen in the KK/Ay mouse model described in Example 11.

EXAMPLE 14
Effects on Insulin-resistance in KK/Ay Mice

KK/Ay mice were administered compound as described in the foregoing Examples. After 2 weeks of treatment, an oral glucose tolerance test (OGTT) was performed in the fasting state by administering a 2 gm/kg glucose solution prepared in deionized water to overnight fasted animals, and measuring venous glucose from the tip of the tail at regularly scheduled time points. In addition, data obtained from young, non-diabetic C57/B16J mice is included for comparison. Calculation of the area under the curve (AUC) displayed in Table 2 was performed using a rectangular summation procedure incorporated within the Prizm data software analysis program (Graphpad, Sorrento, Calif.). The % normalization of the AUC was derived using the following algorithm:

range=vehicle control value−normal value     a).

%=normalization=(vehicle control value−compound treated value)/range.     b).

Treatment of mice with the test compound resulted in a significant normalization of glucose disposal upon challenge.

EXAMPLE 15
Effects on Normoglycemic Insulin-resistance in ob/ob Mice

Female ob/ob mice were administered compound as described above. After 5–6 weeks of dosing, an OGTT was performed as previously described in Example 14. The initial fasting glucose values were obtained from non-diabetic mice. In the absence of prevalent fasting hyperglycemia, as defined by the American Diabetes Association at levels >140 mg/Dl, coupled with a state of insulin-resistance, clinically referred to as Syndrome X, the compound of the present invention elicits a significant normalization of glucose disposal in this state.

All publications and references, including but not limited to patents and patent applications, cited in this specification are herein incorporated by reference in their entirety as if each individual publication or reference were specifically and individually indicated to be incorporated by reference herein as being fully set forth Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed:
1. A compound which is:

2α-propanoyloxy-5,7,8αH-eudesma-4(15),11(13)-dien-8,12-olide;
2α-benzoyloxy-5,7,8αH-eudesma-4(15),11(13)-dien-8,12-olide;
2α-furoyloxy-5,7,8αH-eudesma-4(15),11(13)-dien-8,12-olide;
2α-cyclopropanoyloxy-5,7,8αH-eudesma-4(15),11(13)-dien-8,12-olide;
2α-isobutyryloxy-5,7,8αH-eudesma-4(15),11(13)-dien-8,12-olide;
2α-cyclopropanoyloxy-5,7,8,11αH-eudesm-4(15)-en-8,12-olide;
2α-benzoyloxy-5,7,8,11αH-eudesm-4(15)-en-8,12-olide;
2α-benzoyloxy-4,5,7,8,11αH-eudesman-8,12-olide;
2α-acetoxy-4,5,7,8,11αH-eudesman-8,12-olide;
2α-benzoyl-8β-hydroxy-2β,4,5,7,8,11αH-eudesaman-12-oic acid;
8β-hydroxy-4,5,7,8,11αH-eudesman-12-oic acid;
sodium 8β-hydroxy-5,7,8αH-eudesma-4(15),11(13)-dien-12-oate;
1-[2α-hydroxy-11,12-dihydro-5,7,8αH-eudesm-4(15)-en-8,12-olidyl]-pyrrolidine;
8β-hydroxy-4,7,8αH-eudesama-5,11(13)-dien-12-oic acid;
8β-hydroxy-5,7,8,11αH-eudesam-4(15)-en-12-oic acid;
2α,8β-dihydroxy-2β-4,5,7,8,11αH-eudesaman-12-oic acid;
2α,8β-dihydroxy-4(15)11(13)-eudesamadien-12-oic acid; or a pharmaceutically acceptable salt thereof.

2. A compound which is
2α-propanoyloxy-5,7,8αH-eudesma-4(15),11(13)-dien-8,12-olide or a pharmaceutically acceptable salt thereof.

3. A compound which is
2α-benzoyloxy-5,7,8αH-eudesma-4(15),11(13)-dien-8,12-olide; or a pharmaceutically acceptable salt thereof.

4. A compound which is
2α-furoyloxy-5,7,8αH-eudesma-4(15),11(13)-dien-8,12-olide; or a pharmaceutically acceptable salt thereof.

5. A compound which is
2α-cyclopropanoyloxy-5,7,8αH-eudesma-4(15),11(13)-dien-8,12-olide; or a pharmaceutically acceptable salt thereof.

6. A compound which is
2α-isobutyryloxy-5,7,8αH-eudesma-4(15),11(13)-dien-8,12-olide; or a pharmaceutically acceptable salt thereof.

7. A compound which is
2α-cyclopropanoyloxy-5,7,8,11αH-eudesm-4(15)-en-8,12-olide; or a pharmaceutically acceptable salt thereof.

8. A compound which is
2α-benzoyloxy-5,7,8,11αH-eudesm-4(15)-en-8,12-olide; or a pharmaceutically acceptable salt thereof.

9. A compound which is
2α-benzoyloxy-4,5,7,8,11αH-eudesman-8,12-olide; or a pharmaceutically acceptable salt thereof.

10. A compound which is
2α-acetoxy-4,5,7,8,11αH-eudesman-8,12-olide; or a pharmaceutically acceptable salt thereof.

11. A compound which is
2α-benzoyl-8β-hydroxy-2β,4,5,7,8,11αH-eudesman-12-oic acid; or a pharmaceutically acceptable salt thereof.

12. A compound which is
8β-hydroxy-4,5,7,8,11αH-eudesman-12-oic acid; or a pharmaceutically acceptable salt thereof.

13. A compound which is
sodium 8β-hydroxy-5,7,8αH-eudesma-4(15), 11(13)-dien-12-oate; or a pharmaceutically acceptable salt thereof.

14. A compound which is
1-∂2α-hydroxy-11,12-dihydro-5,7,8αH-eudesm-4(15)-en-, 8,12-olidyl[-pyrrolidine; or a pharmaceutically acceptable salt thereof.

15. A compound which is
8β-hydroxy-4,7,8αH-eudesama-5,11(13)-dien-12-oic acid; or a pharmaceutically acceptable salt thereof.

16. A compound which is 8β-hydroxy-5,7,8,11αH-eudesam-4(15)-en-12-oic acid; or a pharmaceutically acceptable salt thereof.

17. A compound which is 2α,8β-dihydroxy-2β-4,5,7,8,11αH-eudesaman-12-oic acid; or a pharmaceutically acceptable salt thereof.

18. A compound which is 2α,8β-dihydroxy-4(15)11(13)-eudesamadien-12-oic acid; or a pharmaceutically acceptable salt thereof.

* * * * *